United States Patent
Jang (10) Patent No.: US 11,950,891 B2
(45) Date of Patent: Apr. 9, 2024

(54) APPARATUS AND METHOD FOR ESTIMATING BIO-INFORMATION

(71) Applicant: SAMSUNG ELECTRONICS CO., LTD., Suwon-si (KR)

(72) Inventor: Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 271 days.

(21) Appl. No.: 16/547,230

(22) Filed: Aug. 21, 2019

(65) Prior Publication Data

US 2020/0221963 A1  Jul. 16, 2020

(30) Foreign Application Priority Data

Jan. 15, 2019 (KR) .......... 10-2019-0005336

(51) Int. Cl.
*A61B 5/024* (2006.01)
*A61B 5/00* (2006.01)

(52) U.S. Cl.
CPC ........ *A61B 5/02438* (2013.01); *A61B 5/6824* (2013.01); *A61B 5/6831* (2013.01); *A61B 5/7203* (2013.01); *A61B 5/7235* (2013.01)

(58) Field of Classification Search
CPC .............. A61B 5/02438; A61B 5/6824; A61B 5/6831; A61B 5/7203; A61B 5/7235
USPC ........................................................ 600/481
See application file for complete search history.

(56) References Cited

U.S. PATENT DOCUMENTS

| | | |
|---|---|---|
| 5,941,828 A | 8/1999 | Archibald et al. |
| 6,730,038 B2 | 5/2004 | Gallant et al. |
| 7,004,907 B2 | 2/2006 | Banet et al. |
| 7,232,412 B2 | 6/2007 | Shirasaki et al. |
| 8,100,835 B2 | 1/2012 | Baruch |
| 2003/0004421 A1 | 1/2003 | Ting et al. |
| 2004/0147848 A1 | 7/2004 | Shirasaki et al. |
| 2011/0288419 A1 | 11/2011 | Baruch |
| 2014/0066785 A1* | 3/2014 | Watson ............... A61B 5/0285 600/479 |
| 2018/0078215 A1 | 3/2018 | Park et al. |

(Continued)

FOREIGN PATENT DOCUMENTS

| | | |
|---|---|---|
| EP | 1426008 A1 | 6/2004 |
| KR | 10-2016-0028351 A | 3/2016 |

(Continued)

OTHER PUBLICATIONS

Bharati, Subhash, and Girmallappa Gidveer. "Waveform analysis of pulse wave detected in the fingertip with PPG." International journal of advances in engineering & technology 3.1 (2012): 92. (Year: 2012).*

(Continued)

*Primary Examiner* — Eric J Messersmith
*Assistant Examiner* — Chanel J Jhin
(74) *Attorney, Agent, or Firm* — Sughrue Mion, PLLC (57) ABSTRACT

An apparatus for estimating bio-information, includes a pulse wave sensor configured to measure a pulse wave signal from a user, and a processor configured to obtain two or more parameters among a maximum point, an average point, and an onset point, from a waveform of the measured pulse wave signal, and combine the obtained two or more parameters to generate a pulse wave analysis result.

14 Claims, 8 Drawing Sheets

(56) References Cited

U.S. PATENT DOCUMENTS

2019/0029538 A1    1/2019  Jang
2020/0297220 A1*  9/2020  Lu .................. A61B 5/14542

FOREIGN PATENT DOCUMENTS

| KR | 10-1689401 B1 | 12/2016 |
| KR | 10-2018-0031484 A | 3/2018 |

OTHER PUBLICATIONS

Cai, Qing, et al. "Implementation of a wireless pulse oximeter based on wrist band sensor." 2010 3rd International Conference on Biomedical Engineering and Informatics. vol. 5. IEEE, 2010. (Year: 2010).*

Myllylä, Teemu, et al. "Human heart pulse wave responses measured simultaneously at several sensor placements by two MR-compatible fibre optic methods." Journal of Sensors 2012 (2012). (Year: 2012).*

Dae-Geun Jang et al., "Framework for Automatic Delineation of Second Derivative of Photoplethysmogram: A Knowledge-based Approach", Journal of Medical and Biological Engineering, vol. 34 No. 6, 2014, pp. 547-553 (7 pages total).

* cited by examiner

APPARATUS AND METHOD FOR ESTIMATING BIO-INFORMATION

CROSS-REFERENCE TO RELATED APPLICATION

This application claims priority from Korean Patent Application No. 10-2019-0005336, filed on Jan. 15, 2019, in the Korean Intellectual Property Office, the disclosure of which is incorporated herein by reference in its entirety.

BACKGROUND

1. Field

Apparatuses and methods consistent with embodiments relate to technology for estimating bio-information by analyzing a waveform of a pulse wave signal.

2. Description of the Related Art

Recently, with the aging population, soaring medical costs, and a lack of medical personnel for specialized medical services, research is being actively conducted on IT-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or office. Examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, a PPG sensor may estimate blood pressure of a human body by analyzing a shape of pulse waves that reflect a cardiovascular state and the like.

SUMMARY

According to embodiments, there is provided an apparatus for estimating bio-information, the apparatus including a pulse wave sensor configured to measure a pulse wave signal from a user, and a processor configured to obtain two or more parameters among a maximum point, an average point, and an onset point, from a waveform of the measured pulse wave signal, and combine the obtained two or more parameters to generate a pulse wave analysis result.

The pulse wave signal may include any one or any combination of photoplethysmogram (PPG), impedance plethysmogram (IPG), and video plethysmogram (VPG).

The processor may be further configured to obtain, as the average point, any one point of the waveform of the measured pulse wave signal, the any one point being at which a ratio of an area between the maximum point and the any one point to an area between the any one point and the onset point is set to a predetermined ratio.

The processor may be further configured to obtain a representative waveform representing the measured pulse wave signal, and obtain the two or more parameters from the obtained representative waveform.

The processor may be further configured to extract a plurality of one-period signals from the measured pulse wave signal, and obtain any one of the extracted plurality of one-period signals as the representative waveform, or superposing two or more of the extracted plurality of one-period signals to obtain the representative waveform.

The processor may be further configured to, based on the pulse wave signal being measured, perform preprocessing of the measured pulse wave signal, the preprocessing including removing noise from the measured pulse wave signal.

The pulse wave analysis result may include any one or any combination of a ratio between the obtained two or more parameters, a ratio between a value that is obtained by combining the obtained two or more parameters and a remaining one of the obtained two or more parameters, and a ratio between values that are generated by selectively combining the obtained two or more parameters.

The processor may be further configured to, based on the two or more parameters being obtained, generate, as the pulse wave analysis result, a variation in the obtained two or more parameters, based on a reference parameter that is obtained at a time of calibration of the apparatus.

The processor may be further configured to estimate the bio-information, based on the generated pulse wave analysis result.

The bio-information may include any one or any combination of a blood pressure, a vascular compliance, a cardiac output, a total peripheral resistance, and a vascular age.

The apparatus may further include an output interface configured to output either one or both of the generated pulse wave analysis result and the estimated bio-information.

The apparatus may further include a memory configured to store any one or any combination of a reference parameter that is obtained at a time of calibration of the apparatus, the generated pulse wave analysis result, and the estimated bio-information.

According to embodiments, there is provided a method of estimating bio-information, the method including measuring a pulse wave signal from a user, obtaining two or more parameters among a maximum point, an average point, and an onset point, from a waveform of the measured pulse wave signal, and combining the obtained two or more parameters to generate a pulse wave analysis result.

The obtaining of the two or more parameters may include obtaining, as the average point, any one point of the waveform of the measured pulse wave signal, the any one point being at which a ratio of an area between the maximum point and the any one point to an area between the any one point and the onset point is set to a predetermined ratio.

The obtaining of the two or more parameters may include obtaining a representative waveform representing the measured pulse wave signal, and obtaining the two or more parameters from the obtained representative waveform.

The obtaining of the two or more parameters may include extracting a plurality of one-period signals from the measured pulse wave signal, and obtaining any one of the extracted plurality of one-period signals as the representative waveform, or superposing two or more of the extracted plurality of one-period signals to obtain the representative waveform.

The obtaining of the two or more parameters may include, based on the pulse wave signal being measured, performing preprocessing of the measured pulse wave signal, the preprocessing including removing noise from the measured pulse wave signal.

The generating of the pulse wave analysis result may include, based on the two or more parameters being obtained, generating, as the pulse wave analysis result, a variation in the obtained two or more parameters, based on a reference parameter that is obtained at a time of calibration.

The method may further include estimating the bio-information, based on the generated pulse wave analysis result.

The method may further include outputting either one or both of the generated pulse wave analysis result and the estimated bio-information.

DETAILED DESCRIPTION

Details of embodiments are included in the following detailed description and drawings. Advantages and features of the embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module,' etc., may be understood as a unit that performs at least one function or operation and that may be embodied as hardware, software, or a combination thereof.

Hereinafter, embodiments of an apparatus and method for estimating bio-information will be described in detail with reference to the accompanying drawings.

Figure 1:
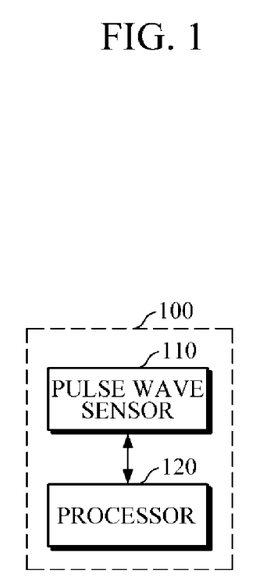
FIGS. 1 and 2 are block diagrams illustrating examples of an apparatus for estimating bio-information, according to embodiments.
Figure 2:
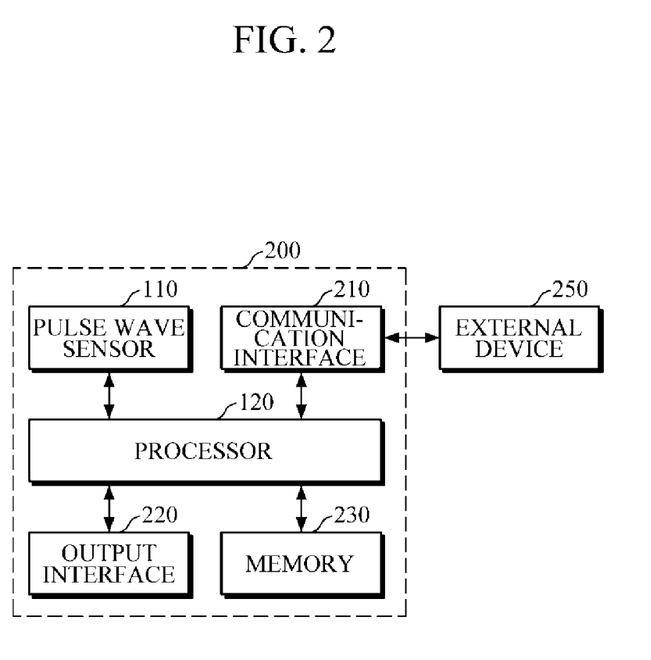

FIGS. 1 and 2 are block diagrams illustrating examples of an apparatus for estimating bio-information, according to embodiments. A bio-information estimating apparatus 100 may be embedded in a terminal, such as a smartphone, a tablet PC, a desktop computer, a laptop computer, and the like, or may be manufactured as an independent hardware device. In this case, the independent hardware device may be a wearable device worn on an object, and examples of the wearable device may include a wristwatch-type wearable device, a bracelet-type wearable device, a wristband-type wearable device, a ring-type wearable device, a glasses-type wearable device, a headband-type wearable device, or the like, but the device is not limited thereto.

Referring to FIG. 1, the bio-information estimating apparatus 100 includes a pulse wave sensor 110 and a processor 120.

The pulse wave sensor 110 may measure a pulse wave signal from an object. In this case, the pulse wave sensor may include a sensor that measures any one or any combination of photoplethysmogram (PPG), impedance plethysmogram (IPG), and video plethysmogram (VPG). For example, the pulse wave sensor, which measures a PPG signal, may include a light source for emitting light onto an object and a detector for detecting light scattered or reflected from the object. In this case, the light source may include a light emitting diode (LED), a laser diode, a fluorescent body, and the like. Further, the detector may include a photo diode, an image sensor, and the like, but is not limited thereto. The light source and/or the detector may be formed as two or more arrays, and each of the light sources may emit light of different wavelengths.

The processor 120 may control various functions of the bio-information estimating apparatus 100. The processor 120 may be electrically connected to the pulse wave sensor 110; and in response to a user' request for estimating bio-information, or in response to occurrence of an event of bio-information estimation according to predetermined criteria, the processor 120 may control the pulse wave sensor 110.

Upon receiving the pulse wave signal from the pulse wave sensor 110, the processor 120 may generate a pulse wave analysis result by analyzing a waveform of the pulse wave signal. Further, the processor 120 may provide the pulse wave analysis result to a user or an external device.

The processor 120 may estimate bio-information based on the pulse wave analysis result, and may provide a bio-information estimation result to a user. In this case, bio-information may include blood pressure, vascular compliance, cardiac output, total peripheral resistance, vascular age, and the like, but is not limited thereto.

Referring to FIG. 2, a bio-information estimating apparatus 200 includes a communication interface 210, an output interface 220, and a memory 230, in addition to the pulse wave sensor 110 and the processor 120 of FIG. 1.

As described above, the pulse wave sensor 110 may include one or more sensors that measure a pulse wave signal such as PPG, IPG, VPG, and the like. The pulse wave sensor 110 may be electrically connected to the processor 120, and may measure a pulse wave signal from a user under the control of the processor 120.

In response to a request for estimating bio-information, the processor 120 may control the pulse wave sensor 110, and may control the communication interface 210, the output interface 220, the memory 230, and the like. Further, upon controlling the communication interface 210 to receive information for estimating bio-information from an external device, the processor 120 may control the memory 230 to store the received information or may control the output interface 220 to output the information. In addition, the processor 120 may refer to the memory 230 to obtain information for estimating bio-information, and may estimate bio-information by using the obtained information.

The communication interface 210 may communicate with an external device 250 to transmit and receive various types of information associated with estimating bio-information. In this case, examples of the external device 250 may include a blood pressure measuring device such as a cuff pressure measuring device, a pulse pressure measuring device, a medical device for measuring other types of bio-information, and an information processing device such as a smartphone, a tablet PC, a desktop computer, a laptop computer, and the like.

For example, the processor 120 may receive reference information (e.g., cuff pressure and bio-information estimation model), which is for estimating blood pressure, from the external device 250. In addition, the processor 120 may transmit pulse wave signal measured by the pulse wave sensor 110, the pulse wave analysis result and the bio-information estimation result that are generated by the processor 120, and the like to the external device 250 such as a user's smartphone, a tablet PC, and the like.

The communication interface 210 may communicate with the external device 250 by using various wired or wireless communication techniques such as Bluetooth communication, Bluetooth Low Energy (BLE) communication, Near Field Communication (NFC), MILAN communication, Zigbee communication, Infrared Data Association (IrDA) communication, Wi-Fi Direct (WFD) communication, Ultra-Wideband (UWB) communication, Ant+ communication, WWI communication, Radio Frequency Identification (RFID) communication, 3G communication, 4G communication, 5G communication, and the like. However, these are examples and are not intended to be limiting.

The output interface 220 may provide the pulse wave signal measured by the pulse wave sensor 110, the pulse wave analysis result and the bio-information estimation result that are processing results of the processor 120, and the like to a user. For example, the output interface 220 may provide a user with information by various visual/non-visual methods using a visual output module such as a display and the like, a voice output module such as a speaker and the like, or a haptic module and the like through vibrations, tactile sensation, and the like.

The memory 230 may store various types of reference information for estimating bio-information, the pulse wave signal measured by the pulse wave sensor 110, the pulse wave analysis result and the bio-information estimation result that are generated by the processor 120, and the like. In this case, the reference information may include user characteristic information including a user's age, sex, health condition and the like, a reference bio-information value obtained at a calibration time, a bio-information estimation model, and the like.

The memory 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3A:
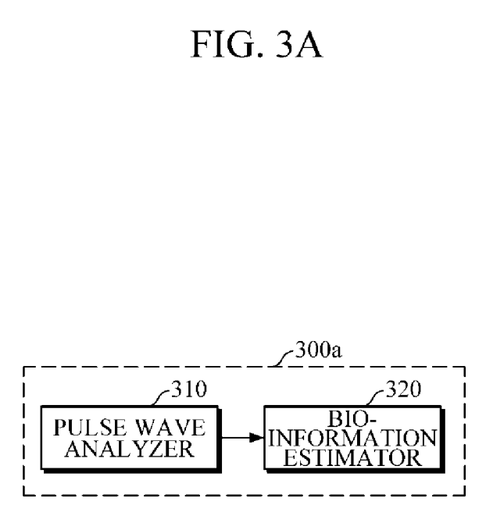
FIGS. 3A and 3B are block diagrams illustrating examples of a processor of FIGS. 1 and 2.
Figure 3B:
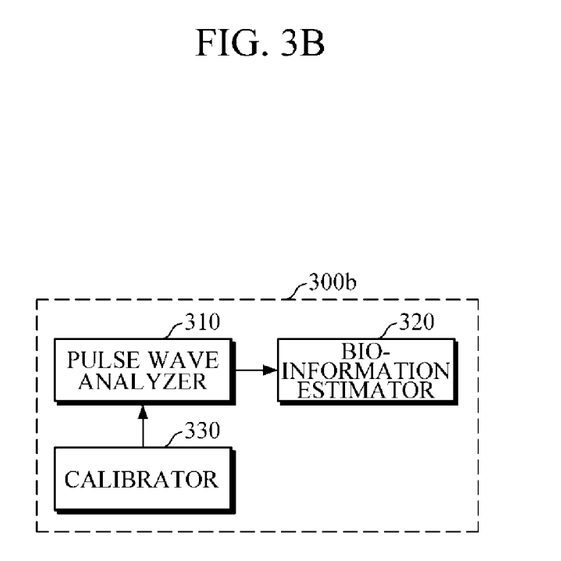
Figure 4A:
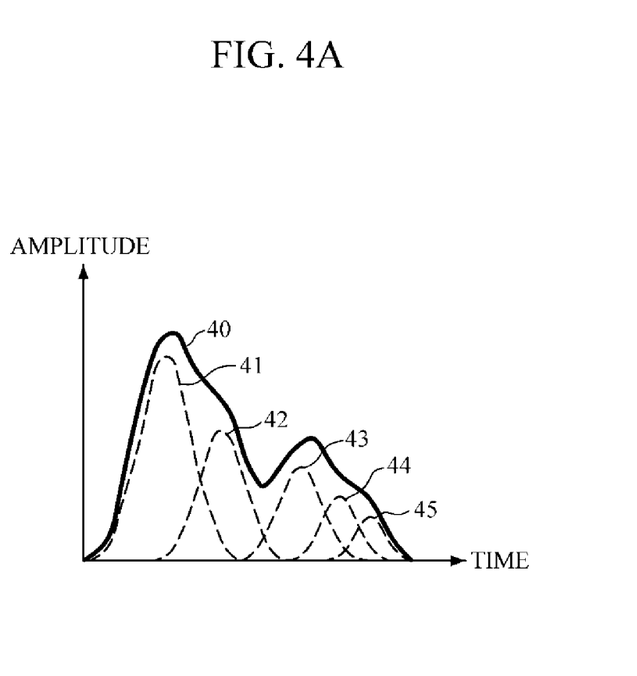
FIGS. 4A to 4B are diagrams explaining an example of estimating bio-information, according to embodiments.
Figure 4B:
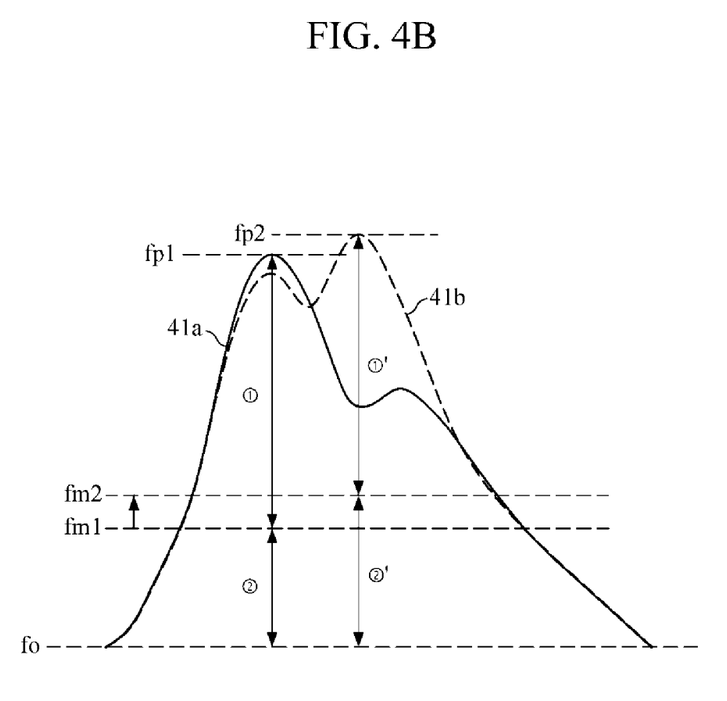

FIGS. 3A and 3B are block diagrams illustrating examples of the processor 120 of FIGS. 1 and 2. FIGS. 4A to 4B are diagrams explaining an example of estimating bio-information, according to embodiments.

Referring to FIG. 3A, a processor 300a includes a pulse wave analyzer 310 and a bio-information estimator 320.

The pulse wave analyzer 310 may receive a pulse wave signal from the pulse wave sensor 110, and may perform preprocessing of the received pulse wave signal, such as removing noise from the pulse wave signal. For example, the pulse wave analyzer 310 may perform preprocessing, such as band-pass filtering between 0.5 Hz to 15 Hz, smoothing, bit equalization of continuously measured signals, and the like.

Further, by analyzing the waveform of the received pulse wave signal, the pulse wave analyzer 310 may generate a pulse wave analysis result for robustly estimating bio-information.

Referring to FIG. 4A, a pulse wave signal 40 is formed by a superposition of a propagation wave 41, starting from the heart toward the distal end portions of the body or branching points in the blood vessels, and reflection waves 42, 43, 44, and 45 returning back from the distal end portions or the branching points of the blood vessels. The propagation wave 41 is related to cardiac characteristics and the reflection waves 42, 43, 44, and 45 are related to vascular characteristics. By using characteristics of the propagation wave 41 and the reflection waves 42, 43, 44, and 45, bio-information such as blood pressure may be estimated.

FIG. 4B is a diagram illustrating an example of a change in an average point of pulse waves and the like according to a change in the amplitude of reflection waves or the time of arrival. Compared to a first pulse wave signal 41a, a second pulse wave signal 41b shows reflection waves that have greater amplitude and arrive later. It can be seen from FIG. 4B that even when the onset points fo of the two signals 41a and 41b are the same, a maximum point fp2 and an average point fm2 of the second pulse wave signal 41b are increased compared to a maximum point fp1 and an average point fm1 of the first pulse wave signal 41a.

Even when a pulse wave feature point is not clearly observed because the amplitude and time of arrival of the reflection waves are changed according to vascular characteristics of a user, the pulse wave analyzer 310 may quantify a change in the pulse wave signal, so that bio-information may be robustly estimated by analyzing the pulse wave signal.

For example, by referring to the first pulse wave signal 41a of FIG. 4B, the pulse wave analyzer 310 may analyze the waveform of the first pulse wave signal 41a to obtain an onset point fo, an average point fm1, and a maximum point fp1 as parameters from the waveform of the first pulse wave signal 41a. In this case, the onset point fo may be a valley amplitude point in an analysis interval of the waveform of the first pulse wave signal 41a. Alternatively, the onset point may refer to points on a straight line formed by connecting a start point and an end point of the analysis interval. For example, an onset point at a time t may be a point corresponding to the time t on the straight line. Further, the maximum point fp1 may be a peak amplitude point in the analysis interval. The average point fm1 may refer to a middle point between the onset point fo and the maximum point fp1; or may be a point, at which a ratio of an area between the maximum point fp1 and the average point fm1 to an area between the average point fm1 and the onset point fo may be set redetermined ratio, e.g., 1:2.

In another example, by referring to the second pulse wave signal 41b of FIG. 4B, the pulse wave analyzer 310 may obtain an onset point fo, an average point fm2, and a maximum point fp2 as parameters from the waveform of the second pulse wave signal 41b.

As described above, the pulse wave analyzer 310 may obtain parameters such as the onset point, the average point, the maximum point, and the like, and may combine the obtained parameters to generate a combination result and/or a pulse wave analysis result for estimating bio-information.

For example, among the point parameter, the average point parameter, and a reference point parameter, the pulse wave analyzer 310 may generate a ratio between two parameters, a ratio between a value, obtained by combining two parameters, and a remaining one of the parameters, a ratio between values generated by selectively combining two parameters, and the like as the pulse wave analysis result. Here, the value obtained by combining two parameters and the values generated by selectively combining two parameters may be values obtained by addition, subtraction, and multiplication of the two parameters, a median value and a mean value of the two parameters, and the like, but are not limited thereto.

Referring to the first pulse wave signal 41a of FIG. 4B, the pulse wave analyzer 310 may generate values, obtained by (fp1−fm1)/(fm1−fo), (fp1−fm1)/(fp1−fo), (fm1−fo)/(fp1−fo), (fo−fm1)/(fp1−fm1), or (fp1−fm1)/(fp1−fm1)(fm1−fo), as the combination result, but is not limited thereto. Referring to the second pulse wave signal 41b of FIG. 4B, the pulse wave analyzer 310 may generate values, obtained by (fp2−fm2)/(fm2−fo), (fp2−fm2)/(fp2−fo), (fm2−fo)/(fp2−fo), (fo−fm2)/(fp2−fm2), or (fp2−fm2)/(fp2−fm2)(fm2−fo), as the combination result.

According to the embodiments as described above, regardless of a shape of the waveform of the pulse wave signal that is affected by the propagation wave, the reflection wave and the like, a change in the waveform of each pulse wave signal may be quantified by using parameters, such as the onset point, the average point, the maximum point, and the like that are obtained from each pulse wave signal, such that the waveform of the pulse wave signal may be robustly analyzed.

Upon receiving the pulse wave signal from the pulse wave sensor 110, the pulse wave analyzer 310 may divide the analysis interval of the pulse wave signal into periods to obtain a plurality of one-period signals, and may obtain any one of the plurality of one-period signals as a representative waveform, or may obtain a representative waveform by superposing two or more of the plurality of one-period signals.

For example, the pulse wave analyzer 310 may determine a one-period signal, having a highest peak amplitude value, among the plurality of one-period signals to be a representative waveform. Alternatively, the pulse wave analyzer 310 may determine a representative waveform by superposing one-period signals having a peak amplitude value that is greater than or equal to a threshold value. Further, by using values obtained by combining two or more parameters among the maximum point, the average point, and the onset point, the pulse wave analyzer 310 may determine, as the representative waveform, any one of the one-period signals having, for example, a largest difference value between the maximum point and the onset point, a largest difference value between the maximum point and the average point, or a largest difference value between the average point and the onset point; or may determine the representative waveform by superposing two or more one-period signals having the difference values that exceed a threshold value.

In another example, the pulse wave analyzer 310 may extract a representative waveform based on a similarity between the plurality of one-period signals. For example, the pulse wave analyzer 310 may determine, as a representative waveform, any one of the one-period signals that has the highest average value of similarities between itself and other one-period signals among the plurality of one-period signals. In addition, the pulse wave analyzer 310 may determine, as a representative waveform, an ensemble average of a predetermined number of one-period signals that have a high average value of similarities between themselves and other one-period signals among the plurality of one-period signals; or may determine, as a representative waveform, an ensemble average of two or more one-period signals having an average value of similarities between themselves and other one-period signals, which is greater than or equal to a predetermined threshold value, among the plurality of one-period signals.

In this case, various similarity calculation algorithms may be used, including Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The bio-information estimator 320 may estimate bio-information based on a pulse wave analysis result generated by the pulse wave analyzer 310.

For example, the bio-information estimator 320 may estimate bio-information by applying a predefined bio-information estimation model. In this case, the bio-information estimation model may be predefined by various methods such as linear/nonlinear regression analysis, neural network, deep learning, and the like.

Referring to FIG. 3B, a processor 300b may further include a calibrator 330 compared to the processor 300a of FIG. 3A.

The calibrator 330 may perform calibration at predetermined intervals, or in response to analysis of a bio-information estimation result or a user's request. Upon determining to perform calibration, the calibrator 330 may control the pulse wave sensor 110 to obtain a pulse wave signal for calibration.

Further, the calibrator 330 may control the communication interface 210 of FIG. 2 to receive reference bio-information, e.g., cuff pressure, which is measured by an external device 250 at a calibration time.

In this case, the calibrator 330 may guide a user to touch the pulse wave sensor 110 with an object, may provide guidance on connection to the external device 250 via the communication interface 210, or may guide a user to measure reference bio-information using the external device 250.

If connection to the external device 250 is not made via the communication interface 210, the calibrator 330 may provide an interface for a user through the output interface 220, and may receive reference bio-information from the user through the interface.

Once the pulse wave sensor 110 measures the pulse wave signal, the calibrator 330 may analyze the measured pulse wave signal to obtain parameters such as the reference point, the average point, the maximum point, and the like as described above. Further, the calibrator 330 may combine the obtained parameters, and may store a pulse wave analysis result in the memory 230 as reference information.

As described above with reference to FIG. 3A, once the calibrator 330 obtains parameters from the pulse wave signal for estimating bio-information or generates the pulse wave analysis result such as a combination result of the parameters, the pulse wave analyzer 310 may obtain a variation in each parameter or the combination result of the parameters by using the reference information stored in the memory 230. The pulse wave analyzer 310 may further generate the obtained variation as a pulse wave analysis result. For example, the pulse wave analyzer 310 may obtain, as the variation, a result of normalization that is performed by dividing each parameter at a bio-information estimation time or a combination result of the parameters by a reference parameter at a calibration time or a combination result of the reference parameters.

The bio-information estimator 320 may estimate bio-information by using the pulse wave analysis result obtained by the pulse wave analyzer 310. For example, the bio-information estimator 320 may estimate a variation of blood pressure by using the pulse wave analysis result, e.g., a variation in the pulse wave analysis result, and a predefined blood pressure variation estimation model. In addition, upon estimating the variation of blood pressure, the bio-information estimator 320 may estimate blood pressure by using a reference blood pressure value obtained at the calibration time.

Figure 5:
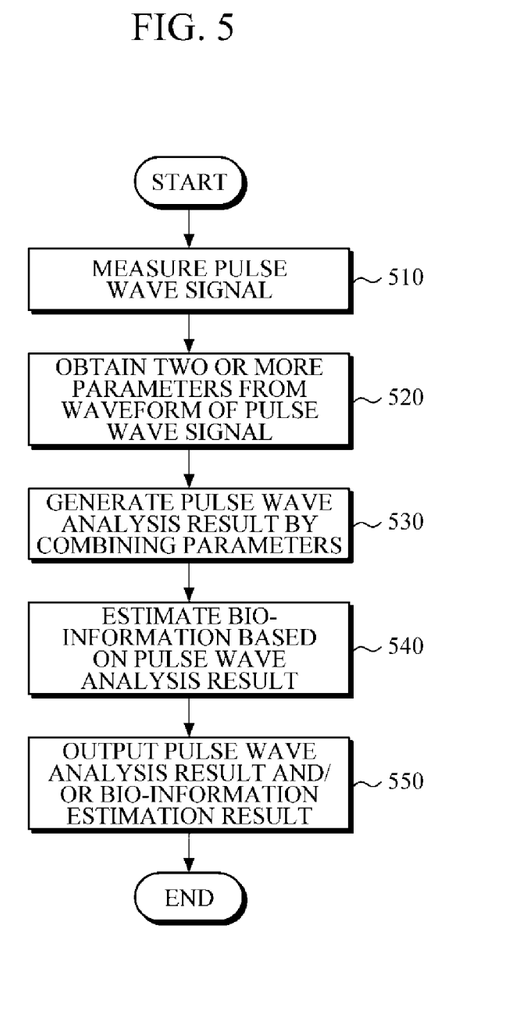
FIG. 5 is a flowchart illustrating a method of estimating bio-information, according to embodiments.

FIG. 5 is a flowchart illustrating a method of estimating bio-information according to embodiments.

The bio-information estimating method of FIG. 5 is an example of a bio-information estimating method according to the embodiments of FIG. 1 or 2.

In response to a request for estimating bio-information, the bio-information estimating apparatus may drive the pulse wave sensor to measure a pulse wave signal in operation 510. The request for estimating bio-information may be input by a user or may be received from a connected external device. Alternatively, for continuous estimation of bio-information, the request for estimating bio-information may be generated at predetermined intervals or may be generated automatically in the bio-information estimating apparatus according to predetermined factors such as a change in external environment and the like. In this case, the pulse wave signal may include any one or any combination of photoplethysmogram (PPG), impedance plethysmogram (IPG), and video plethysmogram (VPG).

Then, the bio-information estimating apparatus may obtain two or more parameters from a waveform of the pulse wave signal in operation 520. For example, the bio-information estimating apparatus may obtain an onset point, an average point, and a maximum point of the waveform of the pulse wave signal as parameters. In addition, the bio-information estimating apparatus may first perform preprocessing including removing noise from the pulse wave signal.

Further, the bio-information estimating apparatus may obtain a plurality of one-period signals by dividing the pulse wave signal in an analysis interval into periods, and may determine a representative waveform among the obtained one-period signals. The bio-information estimating apparatus may obtain parameters, such as the onset point, the average point, the maximum point, and the like, from the determined representative waveform. For example, the bio-information estimating apparatus may determine the representative waveform based on peak amplitude values of the one-period signals, or based on a result of combination of the onset point, the average point, and the maximum point. Alternatively, the bio-information estimating apparatus may also determine the representative waveform based on a similarity between the one-period signals.

Subsequently, the bio-information estimating apparatus may generate a pulse wave analysis result by combining the obtained two or more parameters in operation 530. For example, among a maximum point parameter, an average point parameter, and a reference point parameter, the bio-information estimating apparatus may generate a ratio between two parameters, a ratio between a value obtained by combining two parameters (e.g., values obtained by addition, subtraction, and multiplication of two parameters, a median value and a mean value of the parameters, etc.), and a remaining one parameter, a ratio between values generated by selectively combining two parameters (e.g., values obtained by addition, subtraction, and multiplication of two parameters, a median value and a mean value of the parameters, etc.), and the like as the pulse wave analysis result.

Further, the bio-information estimating apparatus may obtain a variation in each parameter or the combination result of the parameters by using a corresponding reference parameter obtained at a calibration time, or a combination result of reference parameters, and may further generate the obtained variation as the pulse wave analysis result. However, the pulse wave analysis result is not limited thereto, and the bio-information estimating apparatus may generate, as the pulse wave analysis result, various types of information for quantifying the pulse wave signal to robustly analyze the waveform of the pulse wave signal.

Next, the bio-information estimating apparatus may estimate bio-information based on the pulse wave analysis result in operation 540. In this case, the bio-information may include blood pressure, vascular compliance, cardiac output, total peripheral resistance, vascular age, and the like. A model for estimating bio-information may be predefined. For example, for estimating blood pressure, the bio-information estimation model may be a model for immediately estimating blood pressure based on the pulse wave analysis result. Alternatively, the bio-information estimation model may be a model for estimating a variation of blood pressure in comparison with blood pressure at the calibration time. Upon estimating the variation of blood pressure, the bio-information estimation apparatus may also estimate blood pressure by using the blood pressure value at the calibration time as an offset.

Then, the bio-information estimating apparatus may output and provide the pulse wave analysis result and/or the bio-information estimation result to a user in operation 550. For example, the bio-information estimating apparatus may visually provide the results through a display and the like, or may non-visually provide the results through voice, vibrations, tactile sensation, and the like using a speaker, a haptic device, and the like.

Figure 6:
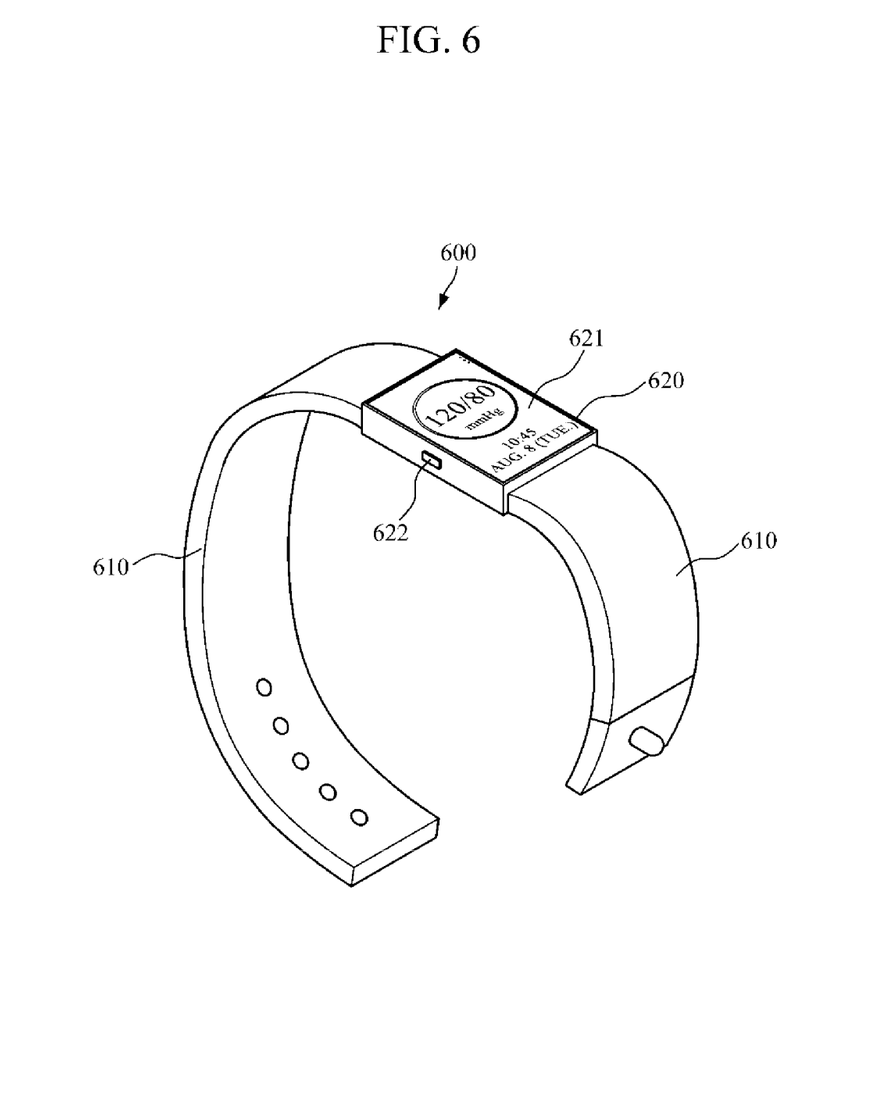
FIG. 6 is a diagram illustrating a wrist-type wearable device according to embodiments.

FIG. 6 is a diagram illustrating a wrist-type wearable device 600 according to embodiments.

Referring to FIG. 6, the wrist-type wearable device 600 includes a strap 610 and a main body 620.

The strap 610 may be connected to both ends of the main body 620 to be fastened in a detachable manner or may be integrally formed therewith as a smart band. The strap 610 may be made of a flexible material to be wrapped around a user's wrist so that the main body 620 may be worn on the wrist.

The main body 620 may include the aforementioned bio-information estimating apparatuses 100 and 200. For example, a pulse wave sensor for measuring a pulse wave signal from a use rise may be mounted in the main body 620. In this case, the pulse wave sensor may be a photoplethysmogram (PPG) sensor that emits light onto the user's wrist, and detects light returning from the user's wrist. However, the sensor is not limited thereto, and may be an impedance plethysmogram (IPG) sensor, a video plethysmogram (VPG) sensor, and the like.

Further, the main body 620 may include a processor that is electrically connected to the pulse wave sensor and measures blood pressure as described above. In addition, the main body 620 may also include a communication interface for communicating with an external device, and a memory for storing information associated with estimating bio-information and other information for performing functions of the wearable device.

A battery, which supplies power to the wrist-type wearable device 600, may be embedded in the main body 620.

The wrist-type wearable device 600 may further include a display 621 and a manipulator 622 that are mounted at the main body 620. The display 621 may display data processed by the wrist-type wearable device 600, processing result data thereof, and the like. The display 621 may include a touch screen that allows touch input, and may receive a touch input from a user and transmit the received input to the processor.

The manipulator 622 may receive input of various control signals from a user. The manipulator 622 may include a power button to turn on/off the wearable device 600.

The embodiments can be realized as a computer-readable code written on a non-transitory computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom decentralized manner. Functional programs, codes, and code segments for realizing the embodiments can be easily deduced by one of ordinary skill in the art.

The inventive concepts have been described herein with regard to the embodiments. However, it will be obvious to those skilled in the art that various changes and modifications can be made without changing technical ideas and features of the disclosure. Thus, it is clear that the above-described embodiments are illustrative in all aspects and are not intended to limit the disclosure.

What is claimed is:

1. A wearable device for estimating bio-information, the wearable device comprising:
a main body having a front surface and a rear surface, wherein the main body includes:
a memory storing a bio-information estimation model,
a communication interface,
an output interface,
a pulse wave sensor, and
a processor configured to:
control the pulse wave sensor to measure a first pulse wave signal from a skin of a user in response to a request for estimating the bio-information while the rear surface of the main body faces the skin of the user, wherein the first pulse wave signal represents a biological condition of the user and the request for estimating the bio-information is automatically generated in the device according to a predetermined factor including a change in an environment external to the device;
perform band-pass filtering on the measured first pulse wave signal in a frequency range to remove noise from the measured first pulse wave signal;
obtain two or more parameters among a maximum point, an onset point, and a point between the maximum point and the onset point, from a waveform of the measured first pulse wave signal;
combine the obtained two or more parameters to generate a first pulse wave analysis result; and
estimate the bio-information for assessing health of the user based on the generated first pulse wave analysis result and the bio-information estimation model stored in the memory,
wherein the bio-information estimation model is a predefined model based on neural network or deep learning,
wherein the pulse wave sensor comprises a photoplethysmogram (PPG) sensor including a light source for emitting light onto the skin facing the rear surface of the main body and a detector for detecting light reflected from the skin facing the rear surface of the main body and measures the first pulse wave signal based on the detected light,
wherein the processor is further configured to:
obtain a plurality of one-period signals from the measured first pulse wave signal;
obtain any one of the obtained plurality of one-period signals as a representative waveform, or superpose two or more of the obtained plurality of one-period signals to obtain the representative waveform; and
obtain the two or more parameters from the obtained representative waveform, and
wherein the processor is further configured to:
perform calibration of the device in response to analysis of the estimated bio-information,
wherein the performing of the calibration comprises:
providing the user with a guidance for touching the PPG sensor and providing the user with a guidance on connection of the wearable device to an external device via the communication interface,
when the wearable device is connected to the external device, controlling the communication interface to receive reference bio-information from the external device,
when the wearable device is not connected to the external device, providing a user interface via the output interface and receiving the reference bio-information from the user, and
controlling the pulse wave sensor to measure a second pulse wave signal for the calibration from the skin facing the rear surface of the main body, obtaining reference parameters corresponding to the two or more parameters from the measured second pulse wave signal for the calibration, combining the obtained reference parameters to generate a second plus wave analysis result, and storing the second plus wave analysis result in the memory as reference information for estimating the bio-information.

2. The wearable device of claim 1, wherein the processor is further configured to obtain, as the point between the maximum point and the onset point, any one point of the waveform of the measured first pulse wave signal, the any one point being at which a ratio of an area between the maximum point and the any one point to an area between the any one point and the onset point is set to a predetermined ratio.

3. The wearable device of claim 1, wherein the processor is further configured to, based on the first pulse wave signal being measured, perform preprocessing of the measured first pulse wave signal, the preprocessing comprising removing noise from the measured first pulse wave signal.

4. The wearable device of claim 1, wherein the first pulse wave analysis result comprises any one or any combination of a ratio between the obtained two or more parameters, a ratio between a value that is obtained by combining the obtained two or more parameters and a remaining one of the obtained two or more parameters, and a ratio between values that are generated by selectively combining the obtained two or more parameters.

5. The wearable device of claim 1, wherein the bio-information comprises any one or any combination of a blood pressure, a vascular compliance, a cardiac output, a total peripheral resistance, and a vascular age.

6. The wearable device of claim 1, wherein the output interface is configured to output either one or both of the generated first pulse wave analysis result and the estimated bio-information.

7. The wearable device of claim 1, wherein the memory is configured to store any one or any combination of a reference parameter that is obtained at a time of the calibration of the device, the generated first pulse wave analysis result, and the estimated bio-information.

8. A wearable device for estimating bio-information, the wearable device comprising:
a main body having a front surface and a rear surface, wherein the main body includes:
a memory storing a bio-information estimation model,
a communication interface,
an output interface,
a pulse wave sensor, and
a processor configured to:
control the pulse wave sensor to measure a first pulse wave signal from a skin of a user in response to a request for estimating the bio-information while the rear surface of the main body faces the skin of the user, wherein the first pulse wave signal represents a biological condition of the user and the request for estimating the bio-information is automatically generated in the device according to a predetermined factor including a change in an environment external to the device;
perform band-pass filtering on the measured first pulse wave signal in a frequency range to remove noise from the measured first pulse wave signal;
obtain two or more parameters among a maximum point, an onset point, and a point between the maximum point and the onset point, from a waveform of the measured first pulse wave signal;
combine the obtained two or more parameters to generate a first pulse wave analysis result; and
estimate the bio-information for assessing health of the user based on the generated first pulse wave analysis result and the bio-information estimation model stored in the memory,
wherein the bio-information estimation model is a predefined model based on neural network or deep learning,
wherein the pulse wave sensor comprises a photoplethysmogram (PPG) sensor including a light source for emitting light onto the skin facing the rear surface of the main body and a detector for detecting light reflected from the skin facing the rear surface of the main body and measures the first pulse wave signal based on the detected light, and
wherein the processor is further configured to, based on the two or more parameters being obtained, generate, as the first pulse wave analysis result, a variation in the obtained two or more parameters, based on a reference parameter obtained at a time of calibration of the device,
wherein the processor is further configured to:
perform the calibration of the device in response to analysis of the estimated bio-information,
wherein the performing of the calibration comprises:
providing the user with a guidance for touching the pulse wave sensor and providing the user a guidance on connection of the wearable device to an external device via the communication interface,
when the wearable device is connected to the external device, controlling the communication interface to receive reference bio-information from the external device,
when the wearable device is not connected to the external device, providing a user interface via the output interface and receiving the reference bio-information from the user,
controlling the pulse wave sensor to measure a second pulse wave signal for the calibration from the skin facing the rear surface of the main body, obtaining reference parameters corresponding to the two or more parameters from the measured second pulse wave signal for the calibration, combining the obtained reference parameters to generate a second plus wave analysis result, and storing the second plus wave analysis result in the memory as reference information for estimating the bio-information.

9. A method of estimating bio-information by a wearable device for estimating the bio-information, the wearable device including a main body having a front surface and a rear surface, the method comprising:
measuring, by a pulse wave sensor of the wearable device for estimating the bio-information, a first pulse wave signal from a skin of a user in response to a request for estimating the bio-information while the rear surface of the main body faces the skin of the user, wherein the first pulse wave signal represents a biological condition of the user and the request for estimating the bio-information is automatically generated in the device according to a predetermined factor including a change in an environment external to the device;
performing band-pass filtering on the measured first pulse wave signal in a frequency range to remove noise from the measured first pulse wave signal;
obtaining, by the device, two or more parameters among a maximum point, an onset point, and a point between the maximum point and the onset point, from a waveform of the measured first pulse wave signal;
combining, by the device, the obtained two or more parameters to generate a first pulse wave analysis result;
estimating, by the device, the bio-information for assessing health of the user based on the generated first pulse wave analysis result and a bio-information estimation model stored in a memory of the device,
wherein the bio-information estimation model is a predefined model based on neural network or deep learning,
wherein the measuring of the first pulse wave signal comprises emitting light onto the skin facing the rear surface of the main body by a light source of a photoplethysmogram (PPG) sensor of the device, detecting light reflected from the skin facing the rear surface of the main body by a detector of the PPG sensor of the device, and measuring the first pulse wave signal based on the detected light, and
wherein the obtaining of the two or more parameters comprises:
obtaining a plurality of one-period signals from the measured first pulse wave signal;
obtaining any one of the obtained plurality of one-period signals as a representative waveform, or superpose two or more of the obtained plurality of one-period signals to obtain the representative waveform; and
obtaining the two or more parameters from the obtained representative waveform,
wherein the method further comprises:
performing calibration of the device in response to analysis of the estimated bio-information, wherein the performing of the calibration comprises:
providing the user with a guidance for touching the pulse wave sensor and providing the user with a guidance on connection of the wearable device to an external device via a communication interface of the device,
when the wearable device is connected to the external device, receiving reference bio-information from the external device via the communication interface,
when the wearable device is not connected to the external device, providing a user interface via an output interface of the device and receiving the reference bio-information from the user, and
measuring, by the pulse wave sensor, a second pulse wave signal for the calibration from the skin facing the rear surface of the main body, obtaining reference parameters corresponding to the two or more parameters from the measured second pulse wave signal for the calibration, combining the obtained reference parameters to generate a second plus wave analysis result, and storing the second plus wave analysis result in the memory as reference information for estimating the bio-information.

10. The method of claim 9, wherein the obtaining of the two or more parameters comprises obtaining, as the point between the maximum point and the onset point, any one point of the waveform of the measured first pulse wave signal, the any one point being at which a ratio of an area between the maximum point and the any one point to an area between the any one point and the onset point is set to a predetermined ratio.

11. The method of claim 9, wherein the obtaining of the two or more parameters comprises, based on the first pulse wave signal being measured, performing preprocessing of the measured first pulse wave signal, the preprocessing comprising removing noise from the measured first pulse wave signal.

12. The method of claim 9, further comprising outputting either one or both of the generated first pulse wave analysis result and the estimated bio-information.

13. The method of claim 9, wherein the bio-information comprises any one or any combination of a blood pressure, a vascular compliance, a cardiac output, a total peripheral resistance, and a vascular age.

14. A method of estimating bio-information by a wearable device for estimating the bio-information, the wearable device including a main body having a front surface and a rear surface, the method comprising:
measuring, by the device for estimating the bio-information, a first pulse wave signal from a skin of a user in response to a request for estimating the bio-information while the rear surface of the main body faces the skin of the user, wherein the first pulse wave signal represents a biological condition of the user and the request for estimating the bio-information is automatically generated in the device according to a predetermined factor including a change in an environment external to the device;

performing band-pass filtering on the measured first pulse wave signal in a frequency range to remove noise from the measured first pulse wave signal;
obtaining, by the device, two or more parameters among a maximum point, an onset point, and a point between the maximum point and the onset point, from a waveform of the measured first pulse wave signal;
combining, by the device, the obtained two or more parameters to generate a first pulse wave analysis result;
estimating, by the device, the bio-information for assessing health of the user based on the generated first pulse wave analysis result and a bio-information estimation model stored in a memory of the device,
wherein the bio-information estimation model is a predefined model based on neural network or deep learning,
wherein the measuring of the first pulse wave signal comprises emitting light onto the skin facing the rear surface of the main body by a light source of a photoplethysmogram (PPG) sensor of the device, detecting light reflected from the skin facing the rear surface of the main body by a detector of the PPG sensor of the device, and measuring the first pulse wave signal based on the detected light, and
wherein the generating of the first pulse wave analysis result comprises, based on the two or more parameters being obtained, generating, as the first pulse wave analysis result, a variation in the obtained two or more parameters, based on a reference parameter obtained at a time of calibration of the device,
wherein the method further comprises:
performing the calibration of the device in response to analysis of the estimated bio-information,
wherein the performing of the calibration comprises:
providing the user with a guidance for touching the PPG sensor and providing the user with a guidance on connection of the wearable device to an external device via a communication interface of the device,
when the wearable device is connected to the external device, receiving reference bio-information from the external device via the communication interface,
when the wearable device is connected to the external device, providing a user interface via an output interface of the device and receiving the reference bio-information from the user, and
measuring, by the device, a second pulse wave signal for the calibration from the skin facing the rear surface of the main body, obtaining reference parameters corresponding to the two or more parameters from the measured second pulse wave signal for the calibration, combining the obtained reference parameters to generate a second plus wave analysis result, and storing the second plus wave analysis result in the memory as reference information for estimating the bio-information.

* * * * *